(12) United States Patent
Ross et al.

(10) Patent No.: US 8,113,427 B2
(45) Date of Patent: Feb. 14, 2012

(54) METHODS AND APPARATUS FOR AUTOMATED PRODUCT IDENTIFICATION IN POINT OF SALE APPLICATIONS

(75) Inventors: Gary Alexander Ross, Scotland (GB); Nart Daghestani, Scotland (GB)

(73) Assignee: NCR Corporation, Duluth, GA (US)

( * ) Notice: Subject to any disclaimer, the term of this patent is extended or adjusted under 35 U.S.C. 154(b) by 491 days.

(21) Appl. No.: 12/338,291

(22) Filed: Dec. 18, 2008

(65) Prior Publication Data

US 2010/0155476 A1    Jun. 24, 2010

(51) Int. Cl.
| | |
|---|---|
| G06K 7/10 | (2006.01) |
| G06K 7/14 | (2006.01) |
| G06K 7/00 | (2006.01) |
| G06K 15/00 | (2006.01) |
| G06K 9/00 | (2006.01) |
| G06K 9/46 | (2006.01) |
| G06K 9/66 | (2006.01) |
| G06Q 20/00 | (2006.01) |

(52) U.S. Cl. .......... 235/454; 235/378; 235/435; 705/64; 705/16; 382/110; 382/181; 382/190; 382/203

(58) Field of Classification Search .................. 235/378, 235/435, 454; 705/64, 16; 382/190, 207, 382/181, 203, 110
See application file for complete search history.

(56) References Cited

U.S. PATENT DOCUMENTS

| | | | | | |
|---|---|---|---|---|---|
| 4,917,500 | A | * | 4/1990 | Lugos | 356/406 |
| 5,182,764 | A | * | 1/1993 | Peschmann et al. | 378/57 |
| 5,546,475 | A | * | 8/1996 | Bolle et al. | 382/190 |
| 6,409,085 | B1 | * | 6/2002 | Gu | 235/462.11 |
| 6,431,446 | B1 | * | 8/2002 | Gu et al. | 235/454 |
| 6,815,683 | B2 | * | 11/2004 | Federici et al. | 250/341.1 |
| 6,845,910 | B2 | * | 1/2005 | Gu et al. | 235/454 |
| 7,275,690 | B1 | * | 10/2007 | White | 235/385 |
| 7,535,005 | B2 | * | 5/2009 | Demers | 250/341.1 |
| 7,633,299 | B2 | * | 12/2009 | Itsuji | 324/639 |
| 2001/0043327 | A1 | * | 11/2001 | Barney et al. | 356/326 |

(Continued)

FOREIGN PATENT DOCUMENTS

EP         2199779 A1 *  6/2010

(Continued)

OTHER PUBLICATIONS

Zolotovskaya S. et al, "Stable dual-wavelength operation of InGaAs diode lasers with volume Bragg gratings" Applied Physics Letters, AIP, American Institute of Physics, Melville, NY, vol. 91, No. 17, Oct. 25, 2007, pp. 171113-171113.

(Continued)

*Primary Examiner* — Daniel Walsh
(74) *Attorney, Agent, or Firm* — Paul W. Martin (57) ABSTRACT

Systems and techniques for product identification using terahertz radiation detection. An area of interest is illuminated with radiation in the terahertz frequency range and terahertz radiation reflected from objects within the area of interest is detected and a detector signal based on the detected radiation is processed to generate identifying information for the objects. The generated identifying information may be compared against stored identifying information for products and the result of the comparison is used to select a product or group of products for which the comparison produces a match. Processing of the detector signal may generate a spectral signature characteristic of reflective and absorptive properties of an object under illumination, and the spectral signature may be compared with stored spectral signature information for products.

22 Claims, 3 Drawing Sheets

U.S. PATENT DOCUMENTS

| | | | |
|---|---|---|---|
| 2002/0179710 A1* | 12/2002 | Gu et al. | 235/454 |
| 2003/0057276 A1* | 3/2003 | Appalucci et al. | 235/382 |
| 2004/0065831 A1* | 4/2004 | Federici et al. | 250/341.1 |
| 2004/0263379 A1* | 12/2004 | Keller | 342/22 |
| 2005/0156110 A1* | 7/2005 | Crawely | 250/338.1 |
| 2005/0231415 A1* | 10/2005 | Fleisher et al. | 342/22 |
| 2005/0232487 A1* | 10/2005 | Fleisher | 382/181 |
| 2006/0054824 A1* | 3/2006 | Federici et al. | 250/339.02 |
| 2006/0231625 A1* | 10/2006 | Cumming et al. | 235/454 |
| 2006/0283931 A1* | 12/2006 | Polli et al. | 235/375 |
| 2007/0085009 A1* | 4/2007 | Adamski | 250/341.8 |
| 2007/0114418 A1* | 5/2007 | Mueller et al. | 250/341.1 |
| 2007/0235650 A1* | 10/2007 | Federici et al. | 250/341.8 |
| 2008/0006767 A1* | 1/2008 | Taday et al. | 250/252.1 |
| 2008/0179527 A1* | 7/2008 | Demers | 250/341.1 |
| 2008/0179528 A1* | 7/2008 | Demers | 250/341.1 |
| 2009/0009190 A1* | 1/2009 | Itsuji | 324/639 |
| 2009/0251286 A1* | 10/2009 | Black et al. | 340/10.1 |
| 2010/0171835 A1* | 7/2010 | Kasai et al. | 348/162 |
| 2010/0206951 A1* | 8/2010 | Herwig | 235/439 |

FOREIGN PATENT DOCUMENTS

GB 2385415 A * 8/2003

OTHER PUBLICATIONS

Venus G. B. et al, "High-brightness narrow-line laser diode source with volume Bragg-grating feedback" Proceedings of the SPIE—The International Society for Optical Engineering, SPIE, US, vol. 5711, Jan. 25, 2005, pp. 166-176.

* cited by examiner

METHODS AND APPARATUS FOR AUTOMATED PRODUCT IDENTIFICATION IN POINT OF SALE APPLICATIONS

FIELD OF THE INVENTION

The present invention relates generally to improvements to point of sale operations. More particularly, the invention relates to improved systems and techniques for automated identification of objects, such as products presented for purchase, using information obtained through the analysis of terahertz (THz) frequency radiation reflected or otherwise emitted from the objects.

BACKGROUND OF THE INVENTION

A pressing issue in point of sale applications has always been the accurate and efficient identification of goods to be sold, and this issue has only become more important with the increase in self service operations and the increased use of automation in both employee assisted and self service operations. Many products are identified through the use of bar code labels or other indicia on or in their packaging, but the use of such indicia is not always convenient. Particularly in the case of produce items, the affixing of identification material interferes with the usability of the product. Today, many produce items sold in supermarkets have label stickers bearing identification codes. These codes are manually input into a terminal at the point of sale, and the stickers are generally removed before the produce is eaten. The affixing of the stickers incurs expense, and the need for their removal frequently annoys the customer and interferes with the customer's enjoyment of the produce. However, the alternatives to labeling each produce item with identifying information have proven more or less unsatisfactory. With the increasing proliferation of different varieties of produce, it is difficult to depend on checkout personnel to consistently and accurately identify each item efficiently, particularly with the increasing use of self checkout facilities. The use of menus and photographs allowing visual matching of items takes time and is not always accurate.

Additional obstacles to accurate identification of produce and other items also exist. Some product packaging may not be conducive to the application of easily readable bar codes, or customers intent on committing fraud may deliberately switch or cover labels or may misidentify products. Many other challenges may be encountered.

SUMMARY OF THE INVENTION

The present invention recognizes and addresses such problems, as well as others, by providing for an automated identification system using terahertz (THz) frequency range energy. THz energy is emitted by numerous objects, and may be detected and processed by a suitable detector. Exemplary mechanisms by which detection may be accomplished include stand-off imaging and sensing, as well as passive imaging. THz energy may also be used to illuminate objects, and the THz energy reflected from these objects may be detected. THz energy is highly sensitive to polar molecules, such as water, and is typically reflected from objects with significant water content, but penetrates many materials such as plastic and cardboard. The evaluation of the dielectric constant at THz frequencies allows estimation of the hydration number. The distinctive features of THz waves, such as their sensitivity to water, may be used to control food and agricultural products. For example, damage to fruit can be evaluated and the water content of vegetables can be monitored. The penetration characteristics of THz radiation vary from one material to another and can be used to provide information about the nature of the material or object from which THz radiation is returned. Each material has a characteristic spectral signature, and these signatures can be stored and correlated to the materials or objects that produce them. When THz waves pass through any of these materials, their photon energy causes them to interact with the material through a number of mechanisms. Because these mechanisms often involve phonons, weak material bond vibrations, and deformations, they are unique to the particular chemical and physical composition of the material. As a result, any internal variations in thickness, density, or chemical composition affect the information content of the terahertz signal. Such information content may include intensity, which is a result of absorption, and phase variations, caused by variations in the refractive index between different materials. For example, measuring absorption as a function of wavelength enables spectroscopic imaging to map chemical composition. In some cases, terahertz radiation can also be used for imaging, and such imaging can be particularly useful in applications in which it is effective, because a number of packaging materials are transparent to such radiation.

The present invention therefore provides for a point of sale terminal using a terahertz radiation analyzer. The point of sale terminal also suitably uses a terahertz radiation source. The terahertz radiation source generates terahertz frequency radiation, which is directed toward a region in which an object may be placed for identification. The terahertz radiation analyzer is positioned and directed so as to receive radiation reflected from or emitted by objects placed within the region. A terahertz radiation detector responds to the radiation that it receives and produces signals in response to this radiation. The signals are interpreted to produce spectral information, and processing resources provided by the analyzer match this spectral information against stored spectral information for known objects. If a proper match is made, the object that has been placed for identification is entered into the transaction. If a match cannot be made, the user or operator of the terminal is notified and given an opportunity to identify the object through other means, such as visually identifying the item and manually providing the information.

A more complete understanding of the present invention, as well as further features and advantages of the invention, will be apparent from the following Detailed Description and the accompanying drawings.

DETAILED DESCRIPTION

Figure 1:
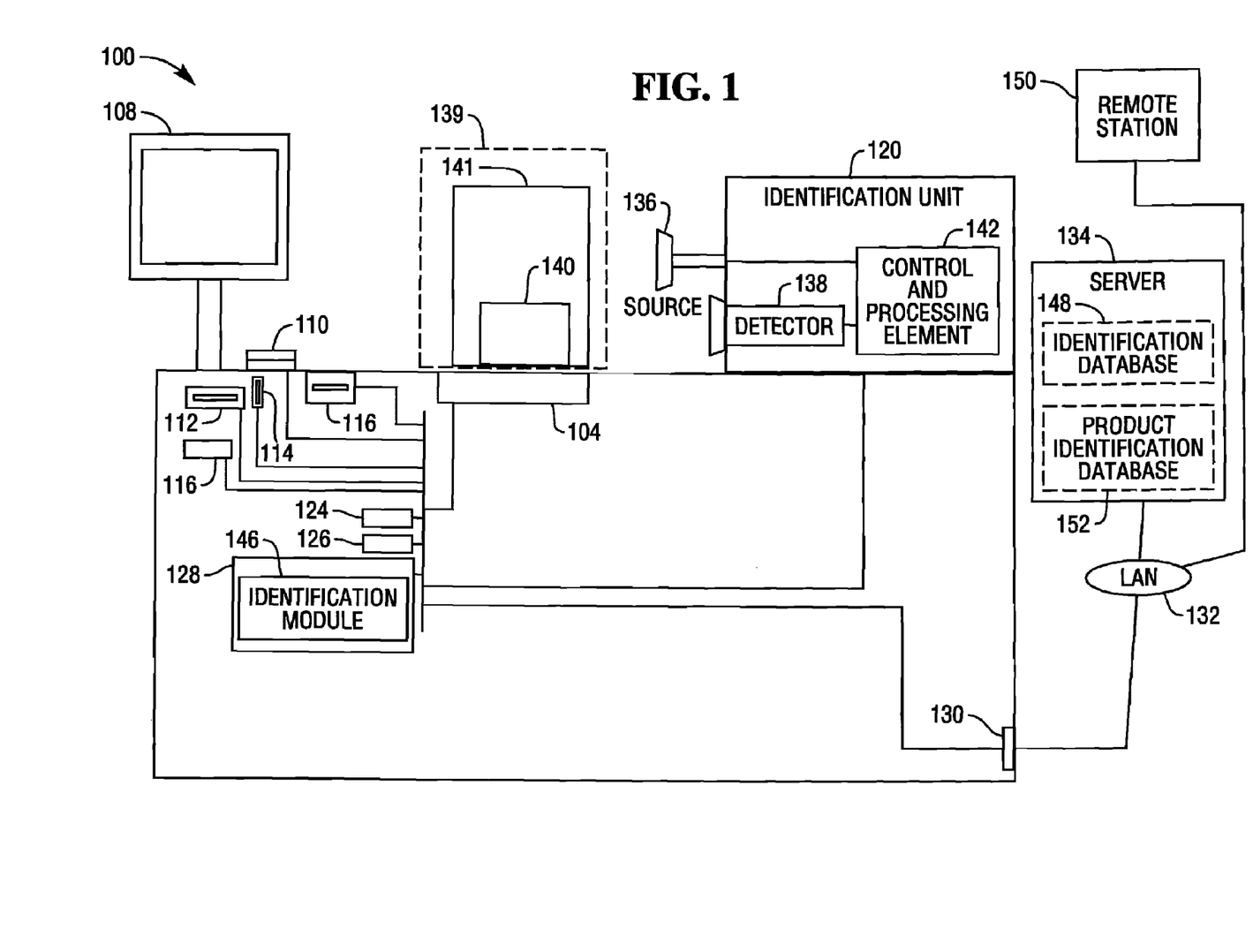
FIG. 1 illustrates a point of sale terminal employing terahertz radiation identification according to an aspect of the present invention.

FIG. 1 illustrates a point of sale terminal 100 according to an aspect of the present invention. The terminal 100 includes a counter 102, a bar code scanner/scale 104, and a display 108, which may be a touch screen display. The terminal 100 also includes a transaction card acceptor 110, a note acceptor 112, a coin acceptor 114, a change dispenser 116, and a receipt printer 118. The terminal 100 also includes a detection and identification unit 120, operating through the illumination of objects with terahertz radiation and the analysis of such radiation to generate identification indicia, such as spectral or image information. Depending on the design of the terminal, identification may be performed by the detection and identification unit 120, or the unit 120 may pass the indicia it produces to other components within the terminal 100 or elsewhere.

The various devices communicate over a bus 122 as needed with one another and with processing hardware that controls the terminal 100 and performs needed information retrieval and processing. The processing hardware includes a processor 124, and computer readable media, such as memory 126 and long term storage 128.

The terminal 100 also includes an external interface 130. The external interface 130 may suitably provide a connection to a network 132, which may include wired and wireless elements, and which mediates communication between the terminal 100 and devices external to the terminal 100, such as a central server 134. The terminal 100 employs the identification unit 120 to generate information that can be used for identification of products presented for sale, as well as other objects that may be subject to identification.

Terahertz frequency radiation is frequently defined as electromagnetic radiation having a frequency in the range of 100 GHz to 3 THz, which is equivalent to a wavelength in the range of 0.1 millimeter (mm) and 3 mm. Such radiation is not ionizing and presents no danger to humans. Terahertz radiation does not penetrate water, but does penetrate many common packaging materials, and the surface and other characteristics of objects that may emit or be illuminated by such radiation cause distinctive differences in the characteristics of the radiation emanating from different types of objects. These differences include distinctive spectral patterns, and these distinctive spectral patterns can be correlated with different object types. Therefore, the identification unit 120 includes a terahertz radiation source 136 and a terahertz radiation detector 138. In the present example, the identification unit 120 is positioned and directed so that an object to be identified may be placed in or moved through a volume 139 to be illuminated by the radiation source 136. A portion of the terahertz radiation reflected from an object 140 within the volume 139 is returned to the radiation detector 138. The object 140 may be placed within a container 141, of a material such as cloth, paper, cardboard, or other material transparent to terahertz radiation. The detector 138 supplies a detector signal to a control and processing element 142, which analyzes the detector signal to generate spectral information. The spectral information may in turn be transferred to the memory 126 and analyzed by the processor 124. The terminal 100 may employ an identification module 146, which may suitably be implemented as software stored on the long term storage 128 and transferred to memory 126 as needed for execution by the processor 124. The identification module 146 may suitably receive the spectral information for an object being identified and compare the received spectral information against stored spectral information for known objects. The stored spectral information may suitably be maintained in an identification database 148, suitably stored on the server 134. The identification database 148 includes spectral information for each of a plurality of products that may be presented for identification. Such spectral information may include detailed information for an element by element match, or may alternatively or in addition include key correlation points such that a smaller number of corresponding points is examined. In addition to examining spectral information for a match to a single item, if such a match cannot be found, the identification module 146 may suitably assemble a list of candidate matches and present these to the user or operator, for example, in the form of a visual menu presented on the display 108. The list of candidate matches is likely to be relatively small, so that a user may be presented with this small number of candidates rather than being required to sort through all the different products that may be available, as would be the case if no such automated identification were performed.

One advantage of such an approach is that terahertz radiation can penetrate numerous packaging materials that are opaque to visible light, or that may distort visible light. Terahertz radiation can easily penetrate plastic or paper bags, as well as cardboard or cloth. Identification could therefore take place without removing products from a container. In addition, the use of terahertz radiation can operate as a check against fraud, or against inadvertent misidentification of products. Two significant aspects of retail fraud are shrouding, in which a higher value product is concealed within packaging for a lower value product and is not entered into a transaction by a customer, and barcode swapping, in which a barcode associated with a lower cost product is affixed to a higher cost product and the product is scanned.

Terahertz radiation can be used to identify the true nature of a product by means of spectral analysis. Such identification can be conducted through packaging or concealing covers, and if the identification of a product does not correspond with the transaction entry, the anomaly can be noted and the transaction suspended until the anomaly is resolved. In addition, terahertz radiation can be used for imaging, and such imaging can be carried out through packaging that is opaque to visible light. Such imaging can be used both for automated product identification and for presentation, such as on the display 108, to show a user or operator the product or products contained in the packaging in the form of a live stream, captured images, or both. Image information may also be delivered to a remote station 150 for review by a remote operator. Additionally, images may be captured for automated image recognition. The image information captured by the identification unit 120 may be captured at any time and this image information may be compared against image information stored in the database 148, which may store a set of terahertz images for each of a plurality of products, as well as the spectral signature information described above. As an image is captured, known reference images are retrieved from the database 148 and the captured image is matched against the reference images. If matching between the captured image and a reference image or set of reference images for a product is determined with sufficient certainty, the product whose image has been captured can be identified as the product associated with the reference images.

Figure 2:
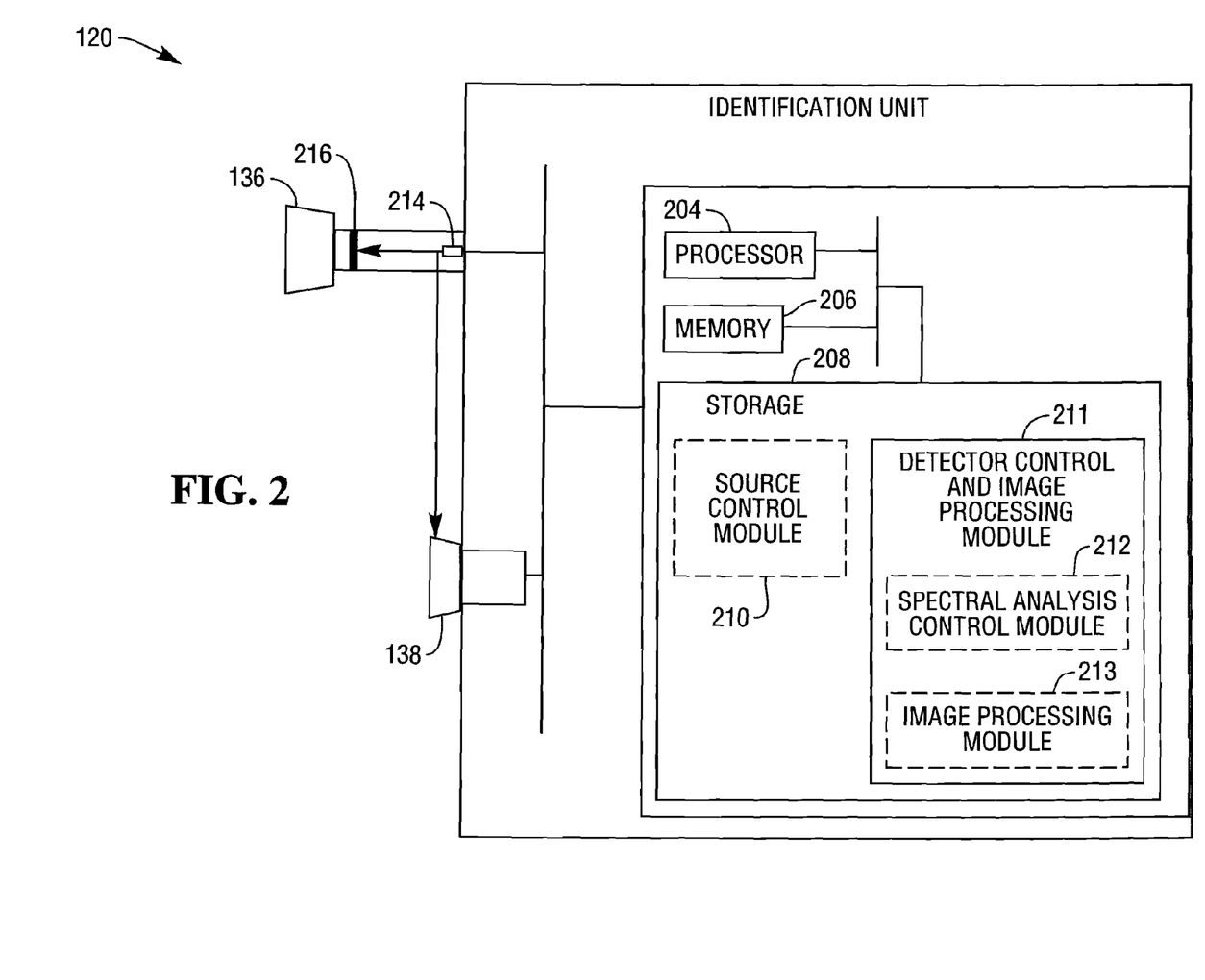
FIG. 2 illustrates a terahertz radiation identifier and analyzer combination according to an aspect of the present invention.

FIG. 2 illustrates additional details of the identification unit 120. The identification unit 120 includes the source 136 and the detector 138, as well as the control and processing element 140. The control and processing element 140 may suitably include a processor 204, high speed memory 206, and storage, such as semipermanent memory 208, storing program instructions and other relatively long term information. Program instructions that may be suitably stored in the semipermanent memory 208 include a source control module 210 for controlling the operation of the source 136, and a detector control and signal processing module 211 for controlling the operation of the detector 138, processing the detector signal to generate spectral data, and supplying this spectral data to processing elements within the terminal 100. The detector control and signal processing module 211 may also comprise a spectral analysis control module 212 and an imaging control module 213. The source control module 210 controls the source 136 to generate radiation of an appropriate frequency range for the action being performed, which is typically spectral analysis or imaging. For spectral analysis, a relatively broad frequency range is preferred, while for imaging a narrower frequency band may be used. The detector control and signal processing module 212 controls the detector 138 so that it is active and correctly configured when radiation is to be detected. Configuration may include, for example, setting sensitivity to a particular frequency or frequency range being used, or setting faster or slower response times. For example, it may be advantageous to differentiate between the frequency range used for spectral analysis as compared to imaging. In addition, spectral analysis can be performed using only a single relatively restricted spot of interest of the object under examination, while imaging requires data from across the extent of the object. Thus, in cases in which spectral analysis is to be performed, the detector 138 may be configured so that only a limited portion of the detector 138 is active, while an imaging application may activate the entire detector.

The detector control and signal processing module 212 also processes the detector signal received from the detector 138. Depending on the action being performed, the signal is processed to generate spectral information that can be compared with spectral information for known objects, or can be processed to generate image information for display or for image recognition.

One particularly useful technique that may be employed in spectral identification is terahertz time domain spectroscopy. The source 136 is controlled so as to probe the object under examination with short pulses of terahertz radiation. The material of the object under examination affects both the phase and the amplitude of the radiation, so that the reflection from the object has phase and amplitude characteristics that are influenced by the object. The terahertz source 136 may suitably comprise a laser 214, emitting a beam passing through a material 216 chosen to emit terahertz radiation in response to stimulation by the laser energy. The energy emitted by the laser 214, and consequently the terahertz radiation emitted by the source 136, typically last a few picoseconds. A single pulse may include frequency components covering the entire terahertz range. One example of a laser that can be employed for the laser 214 is a continuous wave (CW) tunable laser diode with volume Bragg gratings. Such a configuration provides a broad terahertz signal, high peak power, and a very low average power. This configuration differs from prior art continuous wave lasers in that continuous wave lasers generally exhibit high average power consumption, but tuning, which may, for example, involve rotation of a volume Bragg grating, and which may be accomplished using a piezoelectric controller, achieves a reduced average power consumption.

An alternative embodiment of the laser 214 is as an ultrashort pulsed laser. The pulses emitted by the laser 214, and consequently the terahertz radiation emitted by the source 136, typically last a few picoseconds. A single pulse may include frequency components covering the entire terahertz range. Any other configuration emitting appropriate terahertz energy may be employed.

In the present exemplary embodiment, the detector 138 is fed with a portion of the laser energy simultaneously with its emission, and at the same time receives the consequent reflection of the terahertz radiation from the object under examination. The detector 138 produces a different electrical signal depending on whether the detection pulse arrives when the electric field of the terahertz energy is low or high. The electrical signal produced by the detector 138 is sampled and digitized, and a Fourier transform may be used to extract the frequency spectrum from the time domain data.

The operation of the terminal 100 may be better understood through an example. An example of self service operation will be presented here, but it will be recognized that the principles described here are equally applicable to employee assisted operation. The terminal is in an idle state and is activated by a user through an appropriate selection using the display 108. Upon activation, the display 108 may suitably present a menu offering various selections for transaction entries and other relevant operations. The user may be presented with opportunities to scan barcodes, enter codes for products such as produce, identify products through menu selections, or perform other operations. In addition, the user may be given options to simply present items for identification using the identification unit 120. The user may place the items in a designated area for illumination by the radiation source 136, and the radiation reflected by objects within the illumination field of the source 136 is detected by the detector 138.

In one example, the user initiates the transaction and makes various entries through bar code scanning and manual entry. At an appropriate point, the user selects automated identification and is directed to place an object to be identified in the identification area 142. The source 136 illuminates the area 136 with a terahertz wave radiation beam, varying in frequency over a predetermined range calculated to produce the needed spectral information. The source 136 may trace the beam over a prescribed area in order to insure that the beam intercepts the object presented for identification. The object reflects the radiation and a portion of the radiation reflected by the object falls on the detector 138. The detector 138 generates a detector signal, which is processed by the detector control and signal processing module 211. In the present exemplary case, a single object is presented for identification using spectrum generation and comparison, so the detector control and signal processing module 211 processes the detector signal to generate a spectral signature for the object. The spectral signature depends on various distinctive characteristics of the object, with these characteristics involving depth of penetration of the radiation and the strength of reflection across various frequencies.

Once the spectral signature has been generated, a comparison can be made against stored information. The product identification database 148 and the product information database 152 are stored on the central server 134, and the product database 152 may include entries for each product offered. Entries may suitably include appropriate descriptive information for each product, stock number information, universal product code information, pricing information, and other information relevant to managing transactions involving the different products and managing inventory for the products. The spectral information generated by the identification unit 120 is compared against the database 148 and if an identical match is found, information for the identified product may be retrieved from the database 152 and entered into the transaction.

In another exemplary case, the user presents a collection of products for identification in a container that is transparent to terahertz radiation. The products in the container are all of a type that may be detected using terahertz radiation, but need not all be identical. The user indicates that a container holding multiple objects has been presented, and the identification unit 120 initiates operation to identify the objects. First, the identification unit 120 captures an image of the objects within the container. The image that is captured will be used to provide information indicating the placement and separation of the objects, and the number of objects. The imaging may be performed using time domain spectroscopy, but in the case in which imaging is being performed simply to locate objects, the spectra returned from the different objects need not be analyzed. Therefore, if greater speed or efficiency may be gained thereby, illumination and detection may be performed in a way that would not yield accurate identification, because the need at this stage is to determine the presence and extent of an object, rather than to identify the object.

The identification unit 120 thereafter controls the source 136 to emit radiation through the volume in which objects are placed for identification, for example, by sweeping a radiation beam through the volume in an appropriate sequence. As the beam intercepts objects, the reflected radiation is received by the detector 138, and the signal generated by the reflector is processed to indicate the presence or absence of an object at each successive point at which the beam is directed, thereby creating an image sufficient to indicate the presence and shapes of objects in the volume, and their disposition. The image is analyzed to determine the location of each object within the volume and this location information is used to generate targeting information for directing a beam to be used for spectroscopic analysis. One or more target points are selected for each object.

The source 136 is then directed to illuminate the selected target point for each object and a spectral signature is created for each target point for an object by detection and processing of the terahertz radiation reflected from the target point. The spectral signature or signatures for each object are then compared against stored spectral signatures and each object for which a matching signature is found is identified and entered into the transaction. If a match to a single item is not found, it is possible to present possible Snatches to a user for selection, narrowing the range of possibilities with which a user is presented and narrowing the range of choices that a user is called on to make. This approach is made more complex in cases in which multiple different objects are present in the same container or otherwise identified at the same time, because a list of choices may be presented to the user without the user being certain which object the choices relate to. For example, if a box contains different items of produce, the user may have only a vague awareness of which different items are in the container. If several different apples are present in the box and one of the apples is identified as belonging to one of three different varieties of apples, the user may be uninterested in identifying which specific apple is in question and making a decision relating to that specific apple. In such cases, it may be desirable to invite the user to submit the objects one at a time or to identify the objects by other means. However, it is nevertheless possible, especially for a skilled user, such as a retailer employee or a proficient self service customer, to identify the correct candidate from a list of choices even in instances where a number of different objects have been presented, and the terminal 100 may be configured to allow for such operation. One approach is to base this and other operational configurations on indications taken from a user profile, which may be retrieved based, for example, on an employee identifier in the case of employee assisted operation or an identifier such as a frequent shopper card in the case of self service operations.

In addition to being used for identification of products deliberately presented for entry into transactions, the identification unit 120 may also be employed to prevent fraud. Because the identification unit 120 is capable of identifying materials through packaging and identifies an object based on the effect of the material of the object on terahertz radiation, it will be able to detect attempts at fraud conducted through alteration of packaging or labeling, or concealment of objects inside covering materials. The identification unit 120 may therefore be disposed so that it is capable of identifying objects presented at the scanner/scale 104, which is an integrated bar code scanner and weigh scale. The identification unit may also have a field of view encompassing a bagging area 106. It will be recognized that rather than using a single identification unit 120 to provide coverage of the different areas in which fraud detection and prevention may be needed, multiple identification units similar to the unit 120 may be employed. As the user proceeds with transaction entries and movement of items, disparities between the products entered into transactions and the products as they actually appear are noted. Similarly, the presence of products after the conclusion of a transaction can be matched against products entered into a transaction and anomalies noted. For example, a dishonest customer or an employee acting in concert with a customer may exchange a bar code from a lower value product for that of a higher value product, or may simply pass the inauthentic bar code over the scanner while moving the product past the transaction area. A bar code from a bottle of nonalcoholic champagne, for example, may be exchanged for the bar code on bottle of genuine champagne. The products are of similar weight and the improper transaction entry would therefore not be detected by weight verification mechanisms. However, if the identification unit 120 is disposed so as to encompass a view of the scan volume, the actual contents of a package passed over the bar code scanner/scale 104 can be identified. The difference between the actual product and the product as entered into the transaction can be noted and appropriate action taken, such as suspending the transaction for investigation.

In addition or as an alternative to using spectral information, the terminal 100 can use the identification unit 120, or a separate dedicated imaging unit, to perform imaging of objects and can use imaging information as desired, for example, for transmission to an attendant or for automated identification using image recognition. In the present exemplary embodiment, the identification unit 120 is configured and operated so as to perform image recognition. The source control module 210 operates the source 136 in an appropriate frequency range, which may be narrower than that needed for spectral analysis, and directs the source 136 to perform raster scanning of the volume being examined. The detector 138 captures terahertz radiation reflected from objects within the volume being scanned in a similar way to that of a conventional imager. As noted above, many packaging materials are transparent to terahertz radiation, so that the contents of such packaging will be visible. The detector 138 generates a signal responsive to the captured radiation, and the imaging control module 216 manages processing of the signal to produce imaging information. The imaging information may be produced as a live stream, which may be transmitted to a local display in the terminal 100, to a remote station, or both. Additionally or as an alternative, images may be captured for manual or automated review, or for image recognition.

Figure 3:
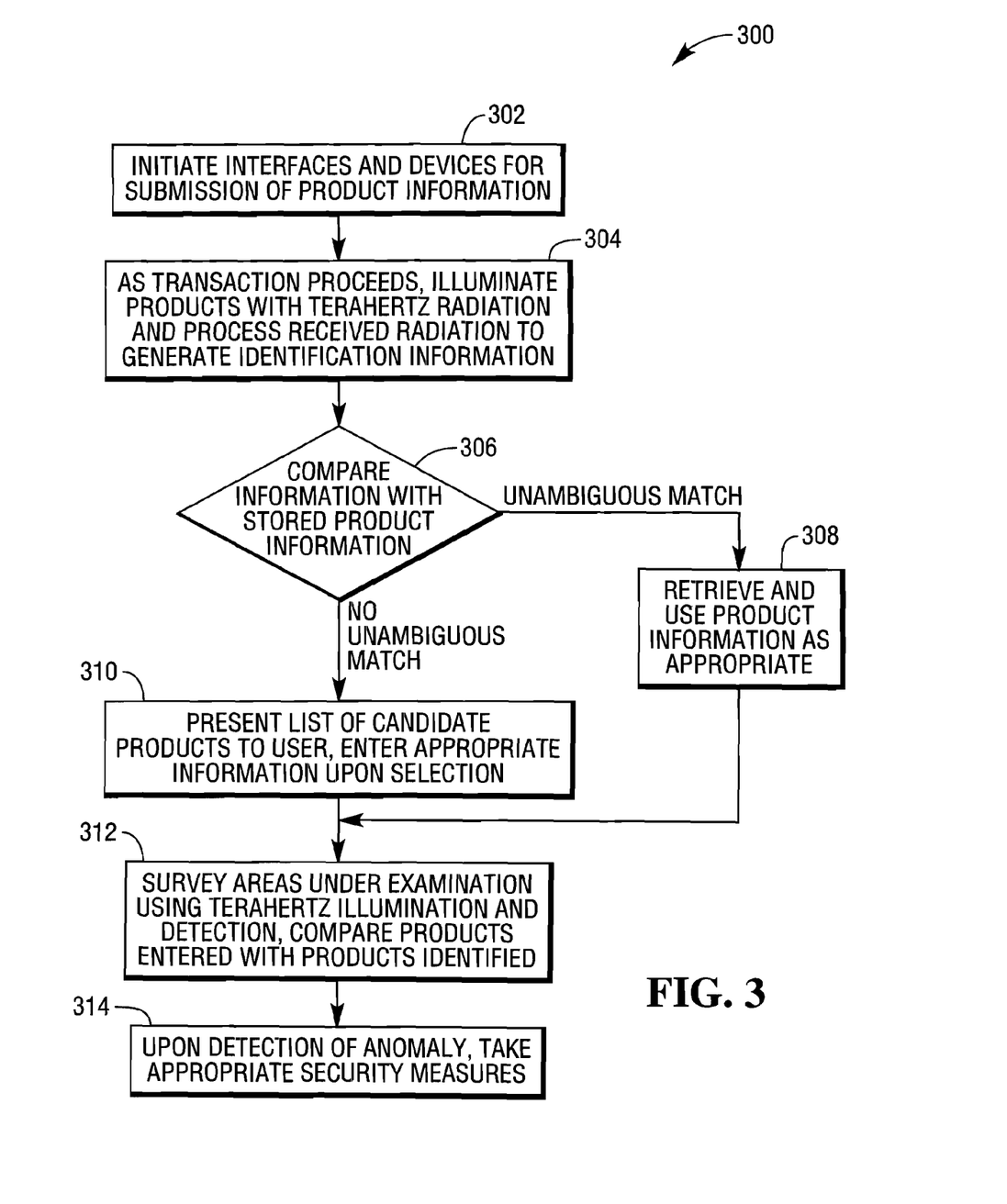
FIG. 3 illustrates a process of identification of products using terahertz radiation radiation according to an aspect of the present invention.

FIG. 3 illustrates the steps of a process 300 of point of sale transaction processing and product identification according to an aspect of the present invention. The process 300 may suitably be conducted using a terminal such as the terminal 100 of FIG. 1 employing an identification unit such as the identification unit 120 of FIGS. 1 and 2. At step 302, at initiation of a transaction by a user, one or more interfaces and devices are activated for submission of product information. Product information may take the form of manual entries, scanned bar code information, or direct submission of products for examination using illumination of the products using terahertz radiation and processing of terahertz radiation reflected by the products to generate information, such as spectral or image information, to identify the products. At step 304, as transactions are processed, objects, such as products being purchased, are placed within a specified area or volume. The products placed within the area or volume are illuminated with terahertz radiation and radiation reflected from the products is processed to generate identification information for the products. The information can be in the form of spectral information representing a spectral signature of the products, image information for the products, or both. At step 306, as image information is obtained for a product, comparisons are made with stored information such as spectral information or image information to identify the objects. If a match to a single item can be made with an object submitted for identification, the process proceeds to step 308 and product information for the product is retrieved and used as appropriate, for example, displaying the product information to a user or attendant, or automatically entering the product information into a transaction. The process then proceeds to step 312. If a match to a single item cannot be made, the process skips to step 310 and a list of candidates representing the nearest matches is made and presented to the user. Upon a selection by the user, appropriate product information for the selected product is entered into the transaction. The process then proceeds to step 312.

At step 312, which may be conducted simultaneously with steps 302-310 discussed above, identification and security information is obtained by examining various areas in which products may be positioned in the vicinity of a point of sale station. Such information may be obtained, for example, by directing the field of illumination of one or more terahertz radiation sources to points of interest and directing the field of view of one or more terahertz radiation detectors to those points of interest. For example, a volume in which products are placed for bar code scanning may be subject to terahertz radiation examination in order to identify the true nature of products being scanned, or a volume in which products that have been entered into a transaction are assembled for removal may be subject to terahertz radiation examination to detect and identify products that have not been entered into a transaction. At step 314, upon detection of an anomaly, suitable action is taken, such as suspending a transaction or issuing a security alert.

While the present invention is disclosed in the context of a presently preferred embodiment, it will be recognized that a wide variety of implementations may be employed by persons of ordinary skill in the art consistent with the above discussion and the claims which follow below.

We claim:

1. A product identification unit comprising:
a terahertz optical radiation source operative to optically illuminate an area of interest with optical terahertz frequency radiation during a purchase transaction at a point of sale (POS) transaction terminal;
a terahertz optical radiation detector operative to detect the illuminated optical terahertz radiation reflected from an object within the area of interest resulting from the optical illumination by the terahertz optical radiation source and operative to generate a detector signal based on the detected optical radiation during the purchase transaction; and
a processor operative to receive a command to identify the object within the area of interest, to operate the terahertz optical radiation source and the terahertz optical radiation detector in response to the command, to process information represented by the detector signal to generate indicia, based on the optical characteristics of the object within the area of interest, wherein the indicia comprises spectral information, to compare the generated indicia to stored reference indicia of products offered for sale in a product identification database, and to send a candidate product to the POS transaction terminal for entry into the purchase transaction, wherein the candidate product is determined to optically correspond to the object of interest, and wherein the processor is operative to complete the purchase transaction at the POS transaction terminal, the purchase transaction comprising at least the object of interest.

2. The product identification unit of claim 1, wherein the indicia include a spectral information signature characteristic of the object, and wherein the spectral information signature is compared against stored spectral information signatures associated with the products.

3. The product identification unit of claim 2, wherein the indicia are generated using terahertz time domain spectroscopy.

4. The product identification unit of claim 3, wherein the terahertz radiation source is a continuous wave tunable laser diode with volume Bragg gratings.

5. The product identification unit of claim 4, wherein the laser diode is tuned through rotation of one or more volume Bragg gratings.

6. The product identification unit of claim 3, wherein the terahertz radiation source is an ultrashort pulsed laser emitting pulses each including frequency components over the entire terahertz spectrum.

7. The product identification unit of claim 2, wherein the processor determines a list of candidate products including the one candidate product.

8. The product identification unit of claim 1, wherein the terahertz radiation source illuminates objects within the area of interest with radiation conducive to generating image information and wherein the processor processes the detector signal so as to generate image information for an object within the area of interest.

9. The product identification unit of claim 8, wherein the image information is sufficient to indicate the presence and locations of one or more objects within the area of interest and wherein the terahertz radiation source directs radiation targeted at each of the objects in order to generate a detector signal for each such object so as to generate a spectral signature characteristic of the object.

10. The product identification unit of claim 9 wherein the spectral signature for each object is compared against stored spectral information signatures associated with the products.

11. A point of sale (POS) transaction terminal, comprising:
a user interface for receiving inputs from a user and furnishing information to a user in order to conduct a point of sale purchase transaction;
a terahertz optical radiation source operative to optically illuminate an area under consideration with terahertz optical radiation during a purchase transaction at the POS terminal;
a terahertz optical radiation detector to detect terahertz optical radiation reflected by one or more objects under the area under optical illumination, and to generate a detection signal based on the detected optical radiation; and a processor, operable to generate, based on the detection signal, identifying data based on optical characteristics comprising spectral data for each of the one or more objects, and operable to identify an object based on comparing the identifying data comprising spectral data to stored reference identifying data comprising spectral data, and operable to enter each of the one or more identified objects into the POS transaction terminal and to complete the purchase transaction comprising the one or more objects.

12. The point of sale terminal of claim 11, wherein the processor is further operative to use the identifying data to identify a product and to examine a transaction record to detect discrepancies between identified products and the transaction record.

13. A method of point of sale (POS) management, comprising the steps of:
  optically illuminating an area of interest in the vicinity of a point of sale terminal with terahertz frequency optical radiation during a purchase transaction;
  detecting terahertz frequency optical radiation reflected from objects within the area of interest as a result of the optical illumination to produce a detection signal based on the detected optical radiation, the purchase transaction including the one or more objects;
  processing the detection signal to generate identifying information based on optical characteristics including spectral information for the objects within the area of interest; and
  comparing the generated identifying information with stored reference spectral identifying information to identify products whose stored reference spectral identifying information matches the generated identifying information,
  and completing the purchase transaction at the POS comprising at least the one or more objects based on the matching.

14. The method of claim 13, wherein the identifying information includes spectral signature information.

15. The method of claim 14, wherein the spectral signature information is generated using terahertz time domain spectroscopy.

16. The method of claim 13, wherein the identifying information includes image information.

17. The method of claim 13, wherein the step of comparing the generated identifying information with stored identifying information comprises identifying near matches between generated identifying information and stored identifying information and further comprising a step of assembling a list of products for which such near matches are identified.

18. The method of claim 17, further comprising a step of presenting the list of products to a user for identification of the product within the area of interest by selecting information for the product from the list.

19. The method of claim 13, further comprising a step of comparing identified products to product information in transaction entries and noting discrepancies between the identified products and the product information in transaction entries.

20. A product identification unit comprising:
  a terahertz optical radiation source operative to optically illuminate an area of interest with optical terahertz frequency radiation during a purchase transaction at a point of sale (POS) transaction terminal, including a continuous wave tunable laser diode with volume Bragg gratings;
  a terahertz optical radiation detector operative to detect the illuminated optical terahertz radiation reflected from an object within the area of interest resulting from the optical illumination by the terahertz optical radiation source and generate a detector signal based on the detected optical radiation during the purchase transaction; and
  a processor operative to process information represented by the detector signal to generate indicia based on optical characteristics including spectral information indicating characteristics of the object within the area of interest so as to allow for comparison of the indicia against a collection of stored reference indicia associated with products offered for sale;
  wherein the indicia are generated using optical terahertz time domain spectroscopy and include a spectral information signature characteristic of the object, and wherein the spectral information signature is compared against stored reference spectral information signatures associated with products in order to identify the product whose associated spectral signature matches the spectral signature generated by the product identification unit; and entering the product into the POS terminal and completing the purchase transaction comprising the object.

21. The product identification unit of claim 1, wherein the object is located within a container at the transaction terminal.

22. A product identification unit comprising:
  a terahertz optical radiation source for generating terahertz frequency optical radiation during a purchase transaction at a point of sale (POS) transaction terminal;
  a terahertz optical radiation detector to detect terahertz optical radiation reflected from within a volume containing an object resulting from optical illumination by the terahertz optical radiation source, and operative to generate a detector signal based on the detected optical radiation during the purchase transaction, the purchase transaction comprising at least the object; and
  a processor operative to cause the terahertz optical radiation source to sweep a beam through the volume, to process first information represented by the detector signal to determine points of the object within the volume, to generate an image from the points, to analyze the image to determine a disposition of the object within the volume, to operate the terahertz optical radiation source to illuminate the object based upon the disposition, to process second information represented by the detector signal to determine a spectral information signature of the object, to compare the spectral information signature to reference spectral information signatures of products offered for sale in a product identification database, and to send a candidate product to the POS transaction terminal for entry into the purchase transaction and to complete the purchase transaction.

* * * * *